United States Patent [19]

Isogai et al.

[11] 4,423,257

[45] Dec. 27, 1983

[54] PROCESS FOR PRODUCING ETHANOL

[75] Inventors: Nobuo Isogai; Motoyuki Hosokawa; Takashi Okawa; Natsuko Wakui; Toshiyasu Watanabe, all of Niigata, Japan

[73] Assignee: Seiichi Ishizaka, President of Agency of Industrial Science and Technology, Tokyo, Japan

[21] Appl. No.: 414,020

[22] Filed: Sep. 2, 1982

[30] Foreign Application Priority Data

Sep. 7, 1981 [JP] Japan .................................. 56-139731

[51] Int. Cl.$^3$ ....................... C07C 31/08; C07C 29/00
[52] U.S. Cl. .................................................... 568/902
[58] Field of Search .......................................... 568/902

[56] References Cited

U.S. PATENT DOCUMENTS

| 4,168,391 | 9/1979 | Slinkard et al. | 568/902 |
| 4,304,946 | 12/1981 | Isogai et al. | 568/902 |
| 4,328,375 | 5/1982 | Barlow | 568/902 |
| 4,355,192 | 10/1982 | Cornils et al. | 568/902 |
| 4,371,724 | 2/1983 | Lin et al. | 568/902 |

*Primary Examiner*—J. E. Evans
*Attorney, Agent, or Firm*—Browdy and Neimark

[57] ABSTRACT

A process for producing ethanol which comprises reacting methanol, carbon monoxide and hydrogen, characterized in that the reaction is carried out in the presence of (a) a solvent selected from the group consisting of hydrocarbons, and ethers and (b) a catalyst comprising a cobalt compound, a ruthenium compound and a tertiary phosphine in the absence of iodine, an iodine compound or a bromine compound is disclosed. According to this invention, ethanol can be produced from methanol, carbon monoxide and hydrogen in a high selectivity to neat ethanol.

9 Claims, No Drawings

PROCESS FOR PRODUCING ETHANOL

BACKGROUND OF THE INVENTION

This invention relates to a process for producing ethanol from methanol, carbon monoxide and hydrogen.

It was known in the prior art that ethanol was produced from methanol, carbon monoxide and hydrogen by using a catalyst comprising a cobalt salt as a main component and iodine, bromine, an iodine compound or a bromine compound and optionally a ruthenium compound or an osmium compound. According to this prior methods, many by-products, such as dimethyl ether, methyl ethyl ether, acetaldehyde, dimethoxy ethane, acetic acid, methyl acetate, ethyl acetate, methyl formate and compounds having $C_3$ or more were produced together with ethanol. That is, selectivity to neat ethanol was insufficient in the prior method.

Use of iodine, bromine, an iodine compound or a bromine compound is critical in the prior method, so corrosion-resistant, expensive material must be used as a material for equipment, when the method is carried out on an industrial scale. In addition, when a cobalt compound, an iodine compound and a ruthenium compound coexist, insoluble material is separated out in the mixture of the starting material and the catalyst and liquid mixture containing the insoluble material can not be fed smoothly into high pressure equipment.

It is desirable that catalysts exhibiting high selectivity to ethanol and not containing iodine, bromine or compounds of these elements be developed for use in a process for industrially producing ethanol from methanol, carbon monoxide and hydrogen.

Catalysts not containing iodine, bromine, an iodine compound or a bromine compound have been proposed for the above purpose, as exemplified in U.S. Pat. No. 4,168,391 patented on Sept. 18, 1979 by Slinkard et al. U.S. Pat. No. 4,168,391 teaches a process for producing ethanol which comprises reacting methanol, carbon monoxide and hydrogen in the presence of a dicobalt octacarbonyl catalyst and an oxygen-containing compound, such as an ester, an alcohol, a ketone, or an ether to form ethanol in reactivity of methanol of 53% and selectivity to ethanol of 69%.

British Patent Application No. 22490/1977 filed on May 27, 1977 teaches reacting methanol, carbon monoxide and hydrogen in the presence of a cobalt compound and a carboxyl group-containing solvent, such as an ester or an organic acid to form ethanol in reactivity of methanol of 36% and selectivity to realizable ethanol of 82.2%.

British Patent Application No. 6291/1978 filed on Feb. 17, 1978 teaches reacting methanol, carbon monoxide and hydrogen in the presence of a cobalt compound and an oxygen-containing compound, such as an aldehyde, a ketone, an alcohol or an ether to form ethanol in reactivity of methanol of 35.1% and selectivity to realizable ethanol of 72.6%.

However, when methanol is reacted with carbon monoxide and hydrogen in the presence of any one of these known catalysts, by-products, such as dimethyl ether, methyl ethyl ether, acetaldehyde, dimethoxy ethane, methyl formate, methyl acetate, ethyl acetate and other compounds of $C_3$ or more other than ethanol (object product) are formed, so selectivity to neat ethanol is low and complicated operation is necessary for separating ethanol from the reaction mixture.

The present inventors repeated the methods disclosed in the above references and always obtained results inferior to the results given in the above references with respect to selectivity to ethanol. Particularly, when an organic acid is used as a solvent as disclosed in British Patent Application No. 22490/1977, the ethanol obtained and the organic acid form an ethyl carboxylate, so the amount of neat ethanol is small. In addition, most of the methanol, which is a starting material, forms a methyl carboxylate with the organic acid. So, a step for separating ethanol from the mixture of ethanol and methanol obtained by hydrolyzing the ethyl carboxylate and the methyl carboxylate is necessary. Therefore, the method is not satisfactory from an industrial point of view.

SUMMARY OF THE INVENTION

The present inventors carried out research for overcoming the shortcomings mentioned above. As a result, we found that when methanol reacts with carbon monoxide and hydrogen in the presence of (a) at least one solvent selected from the group consisting of hydrocarbons, ethers and mixtures thereof and (b) a catalyst comprising a cobalt compound, a ruthenium compound and a tertiary phosphine in atomic ratio of Co:Ru:P is 1:from 0.05 to 0.5:from 0.1 to 2 and in the absence of iodine, or bromine, an iodine compound or a bromine compound, neat ethanol is produced in high selectivity to ethanol.

This invention relates to a process for producing ethanol which comprises reacting methanol, carbon monoxide and hydrogen, characterized in that the reaction is carried out in the presence of (a) at least one solvent selected from the group consisting of hydrocarbons, ethers and mixtures thereof and (b) a catalyst and in the absence of iodine, bromine, an iodine compound or a bromine compound, said catalyst comprising at least one cobalt compound in amount of 1 to 300 milligram atom (mg-atom) in terms of cobalt, at least one ruthenium compound in amount of 0.1 to 100 mg-atom in terms of ruthenium and at least one tertiary phosphine in amount of 2 to 600 mg-atom in terms of phosphorus per 1 mol of methanol, and atomic ratio of cobalt:ruthenium:phosphorus in the catalyst being 1:from 0.05 to 0.5:from 0.1 to 2.

DETAILED EXPLANATION OF THE INVENTION

Use of a cobalt compound, a ruthenium compound and a tertiary phosphine as a catalyst is critical in the present invention. When a two component system catalyst consisting of a cobalt compound and a ruthenium compound is used, the amount of methyl formate by-produced is large and selectivity to ethanol is low.

The cobalt compounds include, for example, cobalt carbonyls, such as dicobalt octacarbonyl and cobalt hydride tetracarbonyl. Synthetic solutions obtained by reacting an inorganic cobalt compound, such as cobalt hydroxide, cobalt carbonate, basic cobalt carbonate or cobalt chloride, or an organic cobalt compound, such as a cobalt organic acid salt, cobaltocene or cobalt acetyl acetonate with synthesis gas containing $H_2$ and CO in methanol, or synthesis solutions obtained by reacting the inorganic cobalt compound or the organic cobalt compound with synthesis gas in the presence of a tertiary phosphine and a hydrocarbon solvent or an ether solvent can also be used as the cobalt compound constituting the catalyst. However, the cobalt compounds exclude cobalt iodide and cobalt bromide. The cobalt compound may be used alone or as a mixture. Dicobalt octacarbonyl is preferable.

The amount of the cobalt compound employed is in the range of 1–300 mg-atom, preferably 5–100 mg-atom in terms of cobalt per 1 mol of methanol. When the amount of cobalt compound is less than the lower limit mentioned above, though the reaction proceeds, the reaction speed is lowered. The use of cobalt compound in an amount of more than the upper limit merely adds to production cost.

The ruthenium compounds include, for example, ruthenium chloride, ruthenium oxide, organic acid salts, such as ruthenium acetate, ruthenocene, ruthenium acetyl acetonate and ruthenium carbonyl. The ruthenium compound may be used alone or as a mixture. The ruthenium compounds exclude ruthenium bromide and ruthenium iodide. Ruthenium chloride is preferable.

The amount of the ruthenium compound employed is in the range of 0.1–100 mg-atom, preferably 1–30 mg-atom in terms of ruthenium per 1 mol of methanol.

The tertiary phosphines of the present invention include, for example, tri-n-butyl phosphine, triphenyl phosphine, tri-p-tolylphosphine, tricyclohexyl phosphine, 1,4-bisdiphenyl phosphinobutane and 1,6-bisdiphenyl phosphinohexane. Tri-n-butyl phosphine is preferable. The amount of the tertiary phosphine employed is in the range of 2–600 mg-atom, perferably 10–200 mg-atom in terms of phosphorus per 1 mol of methanol. The use of the tertiary phosphine in an amount of less than the lower limit as mentioned above is less effective for suppressing formation of methyl formate. The use of tertiary phosphine in an amount of more than the upper limit lowers the reactivity of the methanol and selectivity to ethanol.

The atomic ratio of Co:Ru:P in the catalyst of this invention is in the range of 1:from 0.05 to 0.5:from 0.1 to 2, preferably 1:from 0.1 to 0.4:from 0.5 to 1.5. The catalysts with proportions outside the above ranges increase formation of by-products, such as methyl formate, methyl acetate and ethyl acetate.

The solvents employed in the practice of this invention include hydrocarbon solvents or ether solvents. Hydrocarbon solvents include, for example, aromatic hydrocarbons, such as toluene, benzene and xylene; and aliphatic hydrocarbons, such as hexane and octane. Toluene is particularly preferable. The ether solvents include, for example, diethyl ether, diisopropyl ether, dioxane and tetrahydrofuran. The solvent may be used alone or as a mixture. Toluene is preferable.

The amount of the hydrocarbon or ether solvent employed may be in the range of 0.01–5 mol, preferably 0.1–2 mol per 1 mol of methanol. Use of solvent in an amount of less than the above lower limit decreases the selectivity to ethanol. Use of solvent in an amount of more than the above upper limit lowers the space time yield of ethanol and is not practical. Carbon monoxide and hydrogen may be used in an amount of more than the stoichiometric amount of methanol. The molar ratio of CO to $H_2$ employed may be in the range of 4:1 to 1:4, preferably 2:1 to 1:3.

The reaction pressure may be in the range of more than 50 kg/cm$^2$, and preferably, the pressure is in the range of 150–450 kg/cm$^2$ in the practice of the present invention.

Carbon monoxide and hydrogen employed in the present invention may contain argon, nitrogen, carbon dioxide, methane, ethane and other inert gases. In this case, the total partial pressure of each of carbon monoxide and hydrogen is within the above reaction pressure.

The reaction temperature depends on the catalyst employed and other reaction conditions. In general, the temperature may be in the range of 150°–300° C., preferably 180°–260° C. Though the reaction proceeds at a temperature below 150° C., the reaction speed is low; at temperatures above 300° C. by-products forms.

According to the present invention, ethanol can be produced on an industrial scale from methanol, carbon monoxide and hydrogen without using iodine, bromine, an iodine compound or a bromine compound.

The present invention can be carried out either as batch process or as a continuous process.

The present invention is further illustrated by nonlimiting Examples and Comparative Run.

In the following Examples and Comparative Run, reactivity of methanol, selectivity to ethanol, substantial reactivity of methanol and selectivity to realizable ethanol are expressed by the following equations:

Reactivity of methanol (%) =

$$\frac{\text{mol of CH}_3\text{OH fed} - \text{mol of unreacted CH}_3\text{OH}}{\text{mol of CH}_3\text{OH fed}} \times 100$$

Selectivity to each product (%) =

$$\frac{\text{mol of CH}_3\text{OH converted to each product}}{\text{mol of CH}_3\text{OH fed} - \text{mol of unreacted CH}_3\text{OH}} \times 100$$

Substantial reactivity of methanol (%) =

$$\frac{\text{mol of CH}_3\text{OH fed} - \text{mol of unreacted CH}_3\text{OH} - \text{mol of CH}_3\text{OH converted}^{*1}}{\text{mol of CH}_3\text{OH fed}} \times 100$$

Selectivity to realizable ethanol (%) =

$$\frac{\text{mol of CH}_3\text{OH converted to realizable C}_2\text{H}_5\text{OH}^{*2}}{\text{mol of CH}_3\text{OH fed} - \text{mol of unreacted CH}_3\text{OH} - \text{mol of CH}_3\text{OH converted}} \times 100$$

[*1] contains components, such as dimethoxy methane, methyl esters, etc. from which methanol can easily be recovered through hydrolysis
[*2] contains neat ethanol and components, such as acetaldehyde, dimethoxy ethane, ethyl esters, etc., from which ethanol can easily be recovered through hydrogenation or hydrolysis

EXAMPLE 1

Into a shaking type 100 ml autoclave made of stainless steel were charged 10 gram (g) (0.3121 mol) of methanol, 2 g (0.0058 mol) of dicobalt octacarbonyl, 0.5 g (0.0020 mol) of ruthenium chloride trihydrate, 3 g (0.0148 mol) of tri-n-butyl phosphine and 5 g (0.0543 mol) of toluene. Mixed gas of $H_2$ and CO (molar ratio of 1:1) was fed to pressure of 200 kg/cm$^2$. The reaction was carried out at 210° C. for one hour.

After the reaction, the autoclave was cooled and the gas remaining inside the autoclave was discharged to atmospheric pressure. Gas Chromatograph (GC) Analysis (internal standard method) showed reactivity of methanol of 13.2% and selectivity to neat ethanol of 72.8%. Selectivity to each of the following components was as follows:

| | |
|---|---|
| methyl formate | 5.5% |
| methyl acetate | 5.0% |

| -continued | |
|---|---|
| dimethoxy ethane | 6.9% |

This shows substantial reactivity of methanol of 10.9% and selectivity to realizable ethanol of 85.9%.

EXAMPLE 2

The procedure of Example 1 was repeated except that the reaction time was 3 hours. The results were as follows:

| reactivity of methanol | 22.6% |
|---|---|
| selectivity to neat ethanol | 68.9% |
| selectivity to methyl formate | 3.4% |
| selectivity to methyl acetate | 3.7% |
| selectivity to dimethoxy ethane | 6.4% |

This shows substantial reactivity of methanol of 20.5% and selectivity to realizable ethanol of 78.6%.

Comparative Runs 1-6

The procedures of Example 2 were repeated except that three component catalysts consisting of dicobalt octacarbonyl (main component of the catalyst), ruthenium chloride trihydrate and tri-n-butyl phosphine or toluene as shown in Table 1 is used. The results are shown in Table 1. The lack of four component catalysts (Comparative Run) gives inferior result to use of four component catalysts (Example 2) with respect to selectivity to neat ethanol.

EXAMPLE 3

The procedure of Example 1 was repeated except that 1.0 g (0.0040 mol) of ruthenium chloride trihydrate was used. The results were as follows:

| reactivity of methanol | 16.2% |
|---|---|
| selectivity to neat ethanol | 77.3% |
| selectivity of methyl formate | 4.5% |
| selectivity to methyl acetate | 7.1% |

This shows substantial reactivity of methanol of 14.9% and selectivity to realizable ethanol of 86.2%.

EXAMPLES 4-7

Into a shaking type 100 ml autoclave made of stainless steel weree charged 10 g (0.3121 mol) of methanol, 2 g (0.0058 mol) of dicobalt octacarbonyl, 0.5 g (0.0020 mol) of ruthenium chloride trihydrate, 3 g (0.0148 mol) of tributyl phosphine and each of benzine (Example 4), isooctane (Example 5), dioxane (Example 6) and diisopropyl ether (Example 7) in an amount as shown in Table 2. Mixed gas of $H_2$ and CO (molar ratio of 1:1)was fed to pressure of 200 kg/cm$^2$. The reaction was carried out at 210° C. for 3 hours.

After the reaction, the autoclave was cooled and the gas remaining inside the autoclave was discharged to atmospheric pressure.

GC analysis (internal standard method) gave the results as shown in Table 2.

TABLE 1

| | | Comp. Run 1 | Comp. Run 2 | Comp. Run 3 | Comp. Run 4 | Comp. Run 5 | Comp. Run 6 |
|---|---|---|---|---|---|---|---|
| Co$_2$(CO)$_8$ | g (mol) | 2 (0.0058) | same as the left | same as the left | same as the left | same as the left | same as the left |
| RuCl$_3$.3H$_2$O | g (mol) | — | 0.5 (0.0020) | same as the left | same as the left | — | — |
| tri-n-butyl phosphine | g (mol) | — | — | 3 (0.0148) | — | — | 3 (0.0148) |
| toluene | g (mol) | — | — | — | 5 (0.0543) | same as the left | same as the left |
| reactivity of methanol | % | 25.1 | 29.6 | 27.8 | 21.5 | 15.2 | 5.6 |
| substantial reactivity of methanol | % | 23.2 | 20.9 | 26.9 | 14.5 | 13.9 | 5.2 |
| selectivity to each component (%) | neat ethanol | 43.5 | 23.9 | 53.0 | 32.3 | 50.8 | 52.0 |
| | methyl formate | 2.4 | 15.5 | 0.6 | 30.7 | 7.9 | 6.3 |
| | methyl acetate | 10.0 | 8.7 | 5.5 | 4.2 | 4.3 | 3.4 |
| | ethyl acetate | 5.5 | — | 1.2 | 0.6 | 1.9 | — |
| | dimethoxy ethane | — | — | — | — | — | — |
| | realizable ethanol | 51.4 | 35.1 | 55.4 | 48.6 | 57.6 | 56.5 |

TABLE 2

| | | Example 4 | Example 5 | Example 6 | Example 7 |
|---|---|---|---|---|---|
| solvent | kind | benzene | isooctane | dioxane | diisopropyl ether |
| | g (mol) | 10 (0.1280) | 10 (0.0875) | 10 (0.0567) | (10) (0.0979) |
| reactivity of methanol | % | 27.9 | 27.9 | 31.5 | 18.6 |
| substantial reactivity of methanol | % | 27.0 | 26.6 | 30.1 | 17.5 |
| selectivity to each component (%) | neat ethanol | 65.6 | 60.8 | 61.4 | 60.2 |
| | methyl formate | 2.5 | 2.5 | 1.1 | 5.2 |
| | methyl acetate | 1.6 | 1.4 | 5.1 | 2.1 |

TABLE 2-continued

|  | Example 4 | Example 5 | Example 6 | Example 7 |
|---|---|---|---|---|
| ethyl acetate | 1.2 | — | 2.1 | — |
| dimethoxy ethane | 1.2 | 2.8 | 0.6 | — |
| realizable ethanol | 68.4 | 64.8 | 65.1 | 64.2 |

What is claimed is:

1. A process for producing ethanol which comprises reacting methanol, carbon monoxide and hydrogen, characterized in that the reaction is carried out in the presence of (a) at least one solvent selected from the group consisting of hydrocarbons, ethers and mixtures thereof and (b) a catalyst and in the absence of iodine, bromine, an iodine compound or a bromine compound, said catalyst comprising at least one cobalt compound in amount of 1 to 300 milligram atom (mg-atom) in terms of cobalt, at least one ruthenium compound in amount of 0.1 to 100 mg-atom in terms of ruthenium and at least one tertiary phosphine in amount of 2–600 mg-atom in terms of phosphorus per 1 mol of methanol, and atomic ratio of cobalt:ruthenium:phosphorus in the catalyst being 1:from 0.05 to 0.5:from 0.1 to 2.

2. The process as defined in claim 1 wherein the cobalt compound is dicobalt octacarbonyl.

3. The process as defined in claim 1 wherein the ruthenium compound is ruthenium chloride.

4. The process as defined in claim 1 wherein the tertiary phosphine is tri-n-buthyl phosphine.

5. The process as defined in claim 1 wherein the solvent is toluene.

6. The process as defined in claim 1 wherein solvent is used in amount of 0.01–5 mol per 1 mol of methanol.

7. The process as defined in claim 1 wherein carbon monoxide and hydrogen are used in an amount of more than the stocihiometric amount of methanol.

8. The process as defined in any one of claims 1–7 wherein the reaction pressure is in the range of 50–450 $kg/cm^2$.

9. The process as defined in any one of claims 1–7 wherein the reaction temperature is in the range of 150°–300° C.